United States Patent
Bone et al.

(10) Patent No.: US 10,940,336 B2
(45) Date of Patent: Mar. 9, 2021

(54) METHOD OF ENCAPSULATING A LIQUID ACTIVE

(71) Applicants: GIVAUDAN SA, Vernier (CH); L'UNIVERSITE PIERRE ET MARIE CURIE, Paris (FR); LE CENTRE NATIONAL DE LA RECHERCHE SCIENTIFIQUE, Paris (FR)

(72) Inventors: Stephane Bone, Estouteville Ecalles (FR); Cédric Geffroy, Buxerolles (FR); Sandrine Le Tirilly, Paris (FR); Patrick Perrin, Paris (FR); Claire Vautrin, Pinsot (FR); Cècile Monteux, Paris (FR); Nadége Pantoustier, Paris (FR)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 14/432,077

(22) PCT Filed: Oct. 25, 2013

(86) PCT No.: PCT/EP2013/072397
§ 371 (c)(1),
(2) Date: Mar. 27, 2015

(87) PCT Pub. No.: WO2014/064252
PCT Pub. Date: May 1, 2014

(65) Prior Publication Data
US 2015/0223502 A1    Aug. 13, 2015

(30) Foreign Application Priority Data

Oct. 25, 2012  (EP) .................................. 12290369

(51) Int. Cl.
*A61Q 5/00* (2006.01)
*A61K 8/11* (2006.01)
*C11D 17/00* (2006.01)
*B01J 13/22* (2006.01)
*C11D 3/37* (2006.01)
*A61K 8/81* (2006.01)
*A61Q 19/00* (2006.01)
*A23L 27/00* (2016.01)
*C11B 9/00* (2006.01)

(52) U.S. Cl.
CPC ................ *A61Q 5/00* (2013.01); *A23L 27/72* (2016.08); *A61K 8/11* (2013.01); *A61K 8/8147* (2013.01); *A61K 8/8152* (2013.01); *A61K 8/8176* (2013.01); *A61K 8/8182* (2013.01); *A61Q 19/00* (2013.01); *A61Q 19/007* (2013.01); *B01J 13/22* (2013.01); *C11B 9/00* (2013.01); *C11D 3/3761* (2013.01); *C11D 17/0039* (2013.01); *A23V 2002/00* (2013.01); *A61K 2800/10* (2013.01); *A61K 2800/56* (2013.01); *A61K 2800/594* (2013.01)

(58) Field of Classification Search
CPC .............. C11D 3/3761; C11D 17/0039; A23L 1/22016; A23L 27/72; B01J 13/22; A61Q 19/007; A61Q 19/00; A61Q 5/00; A61K 2800/10; A61K 2800/594; A61K 2800/56; A61K 8/8152; A61K 8/8182; A61K 8/11; A61K 8/8176; A61K 8/8147; C11B 9/00
See application file for complete search history.

(56) References Cited

U.S. PATENT DOCUMENTS

| | | | |
|---|---|---|---|
| 6,740,409 B1 | 5/2004 | Granick et al. | |
| 2005/0163714 A1 | 7/2005 | Sukhishvili et al. | |
| 2006/0051425 A1* | 3/2006 | Kvitnitsky | ........... A61K 9/0014 424/490 |
| 2007/0138671 A1 | 6/2007 | Anastasiou et al. | |
| 2007/0224345 A1* | 9/2007 | Metz | ................... C09B 67/0013 427/212 |

(Continued)

FOREIGN PATENT DOCUMENTS

| | | | |
|---|---|---|---|
| CA | 2593663 A1 | 12/2008 | |
| EP | 0484546 A1 | 5/1992 | |
| EP | 1797947 A2 | 6/2007 | |

(Continued)

OTHER PUBLICATIONS

Wu et al Org Pigm. Part. Coated with Coll. Nano-Silica Part. via lbl 2005 p. 3587.*

(Continued)

*Primary Examiner* — Matthew P Coughlin
*Assistant Examiner* — Thurman Wheeler
(74) *Attorney, Agent, or Firm* — Norris McLaughlin PA

(57) ABSTRACT

A method of encapsulation of an active comprising
(a) dispersing an active in an aqueous medium having a pH of less than 6;
(b) causing the formation on this dispersed active of a polymer shell, the formation comprising the sequential deposition of a series of polymeric layers, each layer being capable of hydrogen bonding with the preceding layer;
to form an aqueous slurry of active-containing capsules; characterised in that one of the first two layers is a polycarboxylic acid and that the first two to four layers taken together exhibit an interfacial compression dilation modulus of greater than 10 mN/m.
The method allows the precise tailoring of polymeric shells, allowing capsules walls to be much thinner without a loss of strength. The technique is especially useful for the encapsulation of fragrances and flavours.

16 Claims, No Drawings

(56) References Cited

U.S. PATENT DOCUMENTS

2009/0047517 A1 2/2009 Caruso et al.
2009/0317792 A1 12/2009 Abbott et al.

FOREIGN PATENT DOCUMENTS

| GB | 2432843 A | 6/2007 |
|---|---|---|
| GB | 2432844 A | 6/2007 |
| GB | 2432850 A | 6/2007 |
| TW | 186559 | 7/1992 |
| WO | 2004016234 A1 | 2/2004 |
| WO | 2005032512 A2 | 4/2005 |
| WO | 2008091228 A2 | 7/2008 |
| WO | 2009138978 A2 | 11/2009 |
| WO | 2010021519 A2 | 2/2010 |

OTHER PUBLICATIONS

Antipov Sustained Rel. Multilayer Capsules, J. Phys. Chem. p. 228 (Year: 2001).*
Grigoriev Encap. Polyelect. LbL Deposition Liq. Core, Langmuir, p. 999, 2008 (Year: 2008).*
International Search Report and Written Opinion of the International Searching Authority for PCT/EP2013/072397 dated May 22, 2014.
GB Search Report for GB 1220746.0 dated Mar. 22, 2013.
Kumar, K N A, et al., "Encapsulation and release of rifampicin using poly(vinyl pyrrolidone)-poly(methacrylic acid) polyelectrolyte capsules", Materials Science and Engineering C, Elsevier Science S.A., CH, vol. 29, No. 8, Oct. 15, 2009, pp. 2508-2513.
Sri Sivakumar, et al., "Degradable, Surfactant-Free, Monodisperse Polymer-Encapsulated Emulsions as Anticancer Drug Carriers", Advanced Materials, John Wiley & Sons, Ltd, vol. 21, Issue 18, pp. 1820-1824, 2009, UK.
Chong, Siow-Feng, et al., "A Paradigm for peptide vaccine delivery using viral epitopes encapsulated in degradable polymer hydrogel capsules", Biomaterials, Elsevier Ltd., 2009, pp. 5178-5186.
Translation of ROC (Taiwan) Search Report for TW Patent Application 10213707 dated May 16, 2017.
TW Search Report for TW Patent/Publication No. TW 186559.
International Search Report and Written Opinion of the International Searching Authority for PCT/EP2013/072403 dated Apr. 25, 2014.
GB Search Report for GB 1220749.4 dated Apr. 2, 2013.
Database WPI week 200978 Thompson Scientific, London, GB; XP002723252 and JP abstract for JP 2009241044, Oct. 22, 2009.
N. Elsner, et al., "pH-Triggered softening of crosslinked hydrogen-bonded capsules", Soft Matter, vol. 2, pp. 966-972, The Royal Society of Chemistry, 2006.

* cited by examiner

METHOD OF ENCAPSULATING A LIQUID ACTIVE

This is an application filed under 35 USC 371 of PCT/EP2013/072397, which claims priority to EP 12290369.3 filed 25 Oct. 2012, the entirety of which documents are herein incorporated by reference.

This disclosure relates to the encapsulation of actives, and particularly fragrances.

Core-shell microcapsules, that is, microcapsules in which a core of a desired active is completely surrounded by a polymeric shell, have been known and used for some time. Typical actives for encapsulation include pharmaceutical and medicinal substances, fragrances and flavours, encapsulation being used for their preservation and later release. Typical examples of uses include, in the fragrance area, fine fragrances, consumer products such as laundry applications including softeners, liquid detergents, and powder detergents; personal care and hair care applications including shampoo, conditioners, combing creams, leave-on conditioners, styling cream, soaps, body creams; deodorants and anti-perspirants; oral care applications, household applications such as cleaning compositions, and in the flavours area, all kinds of consumable compositions (including foodstuffs, beverages and medicinal compositions).

Encapsulation has typically been achieved by emulsifying the active in a solution of shell-forming material and causing the polymer shell to form around the emulsified active particles or droplets. A wide variety of shell materials are known and have been used, for example, gelatine, aminoplast (urea- and melamine-formaldehyde) resins, polyurea polyurethane and acrylic. These typically involve chemical reaction in the formation of the shell, or in its subsequent consolidation, for example, by crosslinking.

It has now been found that an alternative technique may be used successfully to provide encapsulated actives. There is therefore provided a method of encapsulation of active comprising
(a) dispersing an active in an aqueous medium having a pH of less than 6;
(b) causing the formation on this dispersed active of a polymer shell, the formation comprising the sequential deposition of a series of polymeric layers, each layer being capable of hydrogen bonding with the preceding layer;
to form an aqueous slurry of active-containing capsules; characterised in that one of the first two layers is a polycarboxylic acid and that the first two to four layers taken together exhibit an interfacial compression dilation modulus of greater than 10 mN/m.

There is additionally provided encapsulated active, comprising a core of active completely surrounded by a polymeric shell, the shell comprising at least two layers of polymer, each polymer layer being hydrogen-bonded to the adjacent layer(s), and one of the first two layers being a polycarboxylic acid, the first two to four layers taken together exhibiting an interfacial compression dilation modulus of greater than 10 mN/m.

The technique used here is so-called layer-by-layer (LbL) encapsulation. Previously, it has involved the alternate application of two polyelectrolytes to a sacrificial template core (typically silica) to build up a series of layers held together by electrostatic attraction and/or hydrogen bonding. When the desired layers have been attained, the core is then dissolved to give a hollow capsule, which may then be loaded with the desired active. The technique offers the possibility of unprecedented control over release properties, and has been of great interest to the pharmaceutical industry (see, for example, Kozlovskaya et al, *Chem. Mater.* 2006, 18, 328-336).

In this particular application, it has been found possible to make active-containing LbL capsules without any kind of template. To do this, the first two to four layers must comply with a particular physical parameter. This shall be further discussed hereinunder.

The method offers numerous advantages:
1. It does not use any chemical reaction which could leave a residue. Residues can be a problem in some potential uses, for example, in cosmetic and personal care applications. In addition, the polymers used can be selected from polymers that are stable and do not depolymerise to give undesirable species.
2. It allows the precise tailoring of the nature of the capsule shell, and therefore of their robustness and friability, so that breakage at the right time can be assured.
3. It allows robust capsules to be made with shells that are considerably thinner than those made by other techniques. A typical capsule shell made by conventional methods has a thickness of the order of 100-150 nm. Robust shells of thicknesses as low as 5 nm can be made. Typical size ranges are from 5-100, particularly from 5-70, more particularly from 5-50 nm
4. In the specific case of fragrance encapsulation, it allows the preparation of capsules that have a minimal effect on perfumes. It is well known that certain fragrance components, notably aldehydes, have a tendency to react with some encapsulation materials. This can result in the fragrance created by the perfumer not being realised to its full hedonic capacity.

Of the initial two layers of the shell, one must be a polycarboxylic acid. By "polycarboxylic acid" is meant any polymeric material that has a plurality of pendant carboxylic acid groups (which term includes acid anhydrides that become acids under the conditions of the process).

The two layers combine by hydrogen bonding. The phenomenon of hydrogen bonding and the criteria to be fulfilled, so that one material is hydrogen-bonded to another, are well known to the art. In this particular case, there must additionally be adherence to a further parameter, as described hereinunder. Typical combinations include poly (methacrylic acid)/poly(vinyl pyrrolidone), poly(acrylic acid)/poly(vinyl pyrrolidone), poly(vinyl acetate)/ethylene-maleic anhydride copolymer and poly(vinyl alcohol)/ethylene-maleic anhydride copolymer.

Once the initial two layers have been applied, the succeeding layers need not be selected from the same materials as these initial two layers. The only requirement is that each layer hydrogen-bonds with the previous layer. This allows considerable versatility in tailoring the nature of the shell for desired properties.

The shell must be such that the first two to four layers exhibit an interfacial compression dilation modulus of greater than 10 mN/m, preferably greater than 15 mN/m more preferably greater than 20 mN/m. The achievement of this for any given polymer selection is by routine non-inventive experimentation.

The interfacial compression dilation modulus E is given by the equation:

$$E = A_0 \frac{d\gamma}{dA} = \frac{d\gamma}{d\ln A}$$

in which $A_0$ is the initial area of the droplet, A is the area of the droplet and y is the interfacial tension.

The equipment used to measure the interfacial compression dilation modulus is well known to the art. A typical example of a suitable apparatus is a rising/pendant drop tensiometer of the type described in Cao et al in *Journal of Colloid and Interface Science* (2004) 270:295-298.

Examples of an appropriate equipment and method of measurement are further described in detail in the examples hereinunder.

The method of making the capsules consists of applying successive polymer solutions to the active dispersed in aqueous solution. In each layering stage, an excess of polymer is used and the remainder washed away prior to the application of the next layer. This has the advantage that no particular proportions of polymer need be used, so no precise compositional limitations need be observed.

A further advantage of the process is that the high interfacial modulus generated by the polymer association allows the formation of microcapsules with a wide variety of methods such as emulsification, microfluidic or prilling.

The process is simple and robust that allows the achievement of active-bearing capsules having non cross-linked walls of hitherto unobtainable thinness. A typical wall thickness of a melamine-formaldehyde capsule is 150 nm; the thickness here can be as low as 5 nm. Moreover, the process allows the precise tailoring of capsule characteristics, to give an optimum compromise between porosity, robustness (to withstand the rigours of manufacture, compounding, transport and storage) and friability (to allow the capsule to break at the appropriate time and release its active). Moreover, these thin-walled, non-cross-linked microcapsules do not leave any toxic nor sensitive residuals if applied on skin.

The polymer shell may optionally be crosslinked or immobilised. This may be achieved by any convenient means. For example, polymers having amino or hydroxyl groups may be crosslinked by the addition of materials such as amines, glutaraldehyde, isocyanates, epoxides or silicate coupling agents having such a reactive function. Alternatively, there may be provided a final layer of silicate. This is provided by the hydrolysis of $(R)_n Si(ROH)_4$, in which R is C1-C3 alkyl and n=1-4, and the addition of the hydrolysis product to the slurry of LbL capsules.

The polymer shell may optionally be used as a basis for further chemistry in order to obtain aminoplast, polyurea, polyurethane, polyacrylic or inorganic microcapsules, by depositing such materials on the shell.

The capsules prepared as hereinabove described may be used in many different applications. Typical examples of commercial compositions (i.e., compositions sold for particular consumer or industrial end-uses) include (i) in the fragrance industry, fine fragrances, consumer products such as laundry applications including softeners, liquid detergents, and powder detergents; personal care and hair care applications including shampoo, conditioners, combing creams, leave-on conditioners, styling cream, soaps, body creams; deodorants and anti-perspirants; oral care applications, such as toothpastes and mouthwashes, household applications such as cleaning compositions, medicinal products;

(ii) in the flavours industry, all kinds of consumable compositions, such as canned and instant soups, prepackaged meals, frozen foods, frozen desserts, baked goods, beverages, dairy products;

(iii) in the medicinal area, all manner of pharmaceutical and medicinal substances.

It is naturally possible to include more than one active.

There is therefore also provided a commercial composition comprising a commercial composition base and an encapsulated active, the active being contained in capsules prepared as hereinabove described. By "commercial product base" is meant all the art-recognised ingredients normally used in the particular composition. The natures and proportions of these will vary according to the nature of the composition, but all such formulation is within the ordinary skill of the art.

The quantity of capsules added will depend entirely on the end-use and the nature of the composition. Given the wide variety of such end-uses and compositions, the possible proportions involved are equally wide, but a suitable proportion can always be ascertained by non-inventive, routine experimentation.

The disclosure is further described with reference to the following non-limiting examples, which depict particular embodiments.

EXAMPLE 1

Method of Measurement of Interfacial Compression Dilation Modulus

The interfacial compression dilation modulus is measured using a rising/pendant drop tensiometer of the type described in Cao et al in *Journal of Colloid and Interface Science* (2004) 270:295-298.

1. Preparation of polymer solution at 1 wt % in water
   a. The polymer is dissolved in Milli-Q Water at 2 wt %. Millipore (Milli-Q system) filtered water with an 18.2 MO resistivity is used
   b. The solution is stirred for at least 12 h
   c. The pH of the polymer solution is adjusted to 3 with 1M NaOH or 1M HCl
   d. Water is added until a 1wt % polymer solution is obtained.
2. Preparation of the rinsing solution: Millipore water is adjusted to pH 3 with 1M HCl
3. Layer construction at the oil/water interface
   a. 5 mL of a solution of a first polymer (Polymer A) is introduced into the cell
   b. A drop of fragrance is formed in the cell at the end of a needle (drop volume depending on the system)
   c. A waiting time of 1 h to 12 h enables the polymer adsorption at the oil-water interface
   d. The aqueous phase in the cell is rinsed with the rinsing solution to remove excess polymer. The rinsing is done with a bulk phase exchange. There is a flow of 10 mL/min for 15 min.
   e. 15 min. wait
   f. The aqueous phase in the cell is then rinsed with a second polymer solution (Polymer B). The rinsing is done with a bulk phase exchange. There is a flow of 10 mL/min for 5 min.
   g. A waiting time of 25 min to 1 h enables the second polymer adsorption at the oil-water interface
   h. The method is repeated until the desired number of layers at the oil-water interface is achieved.
4. Measurement of the interfacial dilation-compression modulus
   a. Once the layers are adsorbed, the measurement is carried out b. Area oscillations are run for frequency of 0.1 Hz for area deformation from 0.1 to 10%
c. Values of interfacial compression dilation modulus are calculated according to the equation given above.

EXAMPLE 2

Preparation of Fragrance-Containing Capsules

The polymers used in this are poly(methacrylic acid) and poly(vinyl pyrrolidone). 2 layers, when measured by the method outlined hereinabove, exhibit a interfacial compression dilation modulus of 150 mN/m.

A 5 mL of a 1% (wt) PMAA aqueous solution is adjusted to pH 3. To this solution is added 5 mL of a proprietary fragrance. The two solutions are kept in contact for 24 hours, then emulsified using an Ultra-turrax™ blender at 24000 rpm for 2 minutes. The emulsion is added to a separating funnel and washed with water at pH 3 ($10^{-3}$ M HCl) to give a 10% fragrance solution.

This solution is slowly mixed and then allowed to settle for 24 hours.

The lower aqueous phase is removed and washed four times to extract excess polymer. This washed phase is added to 1 (wt) % aqueous PVP solution at pH3 under gently stirring. This phase is allowed to settle for 24 h and it is then washed with water at pH 3 as described in the previous step. The settling, lower layer removal and washing steps are repeated.

The previous step is repeated with PMAA solution, and then again with PVP solution. This alternation is continued until 5 layers have been deposited. After 2 layers, microcapsules can be observed under the microscope, and they are sufficiently strong to retain their integrity.

The final fragrance-containing capsules have an average diameter of 31 μm and a wall thickness of 14 nm.

EXAMPLE 3

Preparation of Fragrance-Containing Capsules

The polymers used in this example are 50PAA1C12 and poly(vinyl pyrrolidone). 50PAA1C12 is a polyacrylic acid with some hydrophobic constituents: the backbone is about 50 000 g/mol. The grafted part has 12 carbons and it is grafted at 1 (mol) % (1 hydrophobic part for 100 units).

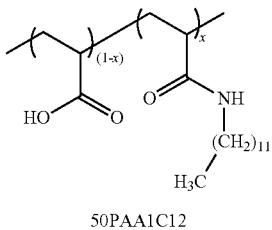

50PAA1C12

When deposited as 4 layers, the interfacial compression dilation modulus is 40 mN/m.

A 5 mL of a 1% (wt) 50PAA1C12 aqueous solution is adjusted to pH 3. To this solution is added 5 mL of a proprietary fragrance. The two solutions are kept in contact for 24 hours, then emulsified using an Ultra-turrax™ blender at 24000 rpm for 2 minutes. The emulsion is added to a separating funnel and washed with water at pH 3 ($10^{-3}$ M HCl) to give a 10% fragrance solution.

This solution is slowly mixed and then allowed to settle for 24 hours.

The lower aqueous phase is removed and washed four times to extract excess polymer. This washed phase is added to 1 (wt) % aqueous PVP solution at pH3 under gently stirring. This phase is allowed to settle for 24 h and it is then washed with water at pH 3 as described in the previous step. The settling, lower layer removal and washing steps are repeated.

The previous step is repeated with PAA solution, and then again with PVP solution. This alternation is continued until a desired number of layers is attained, in this case until 5 layers are attained. After 2 layers, microcapsules can be observed under the microscope and manipulated.

The final fragrance-containing capsules have an average diameter of 31 μm and a wall thickness of 18 nm.

EXAMPLE 4

Testing of Microcapsules

PMAA/PVP microcapsules of the type described in Example 2, but with 10 layers, are deposited on a blotter. To another blotter is added proprietary fragrance of the type in the capsules, such that the quantity of fragrance added is the same.

The blotters are left to stand for 24 hours at 25° C. and normal atmospheric pressure, and they are evaluated by a team of 8 trained fragrance panellists.

The panellists found that the odour in both cases is weak and the same intensity. However, rubbing the blotter with the capsules produced a noticeable boost in fragrance.

EXAMPLE 5

Preparation of a Body Cream Comprising 10-Layer PMAA/PVP Microcapsules of the Type Described in Example 2

A body cream formulation is prepared by admixing the ingredients listed in the table.

| Ingredient | Amount [%] w/w |
| --- | --- |
| Petrolatum oil | 5 |
| Cetyl Alcohol | 0.5 |
| Cetearyl Octonoate | 1 |
| Stearic acid | 0.5 |
| Isopropyl palmitate | 3 |
| Isopropyl myristate | 2 |
| Steareth 2 (surfactant) | 2.9 |
| Steareth 21 (surfactant) | 2.1 |
| Methyl Paraben (Preservative) | 0.2 |
| Propyl Paraben (Preservative) | 0.1 |
| Carbomer 980 (Thickener) | 0.2 |
| Sodium hydroxide (10%) | to pH = 5.7 |
| Deionised water | 82.5 |

Body cream is prepared by mixing the microcapsules at 2% by weight, relative to the total weight of the body cream into the body cream formulation shown in the table. To the identical body cream is added a proprietary fragrance of the type in the capsules, such that the quantity of fragrance added is the same.

Body creams are applied to human skin on the forearm, in an amount of 0.5 g with a micropipette, and the forearm is gently massaged during 10 sec by rubbing a finger on the whole surface.

The perfume intensity is evaluated on a blind basis after 4 hours by an expert panel consisting of 8 trained panellists. The panellists find that the odour in both cases is weak and have the same intensity. However, rubbing the forearm with the capsules produces a noticeable boost in fragrance.

EXAMPLE 6

Preparation of a Flavour-Shifting Ice Cream Comprising 10-Layer PMAA/PVP Microcapsules of Example 2

An ice cream is prepared by mixing the microcapsules containing a cherry flavour into an ice cream formulation at pH 5 containing a vanilla flavour.

The initial taste sensation is vanilla, quickly followed by cherry flavour after dissolution of capsules at pH 7 in the mouth.

EXAMPLE 7

Preparation of a Leave-on Hair Cream Formulation Comprising 10-Layer PMAA/PVP Microcapsules of Example 2

A leave-on formulation is prepared by admixing the ingredients listed in the table.

| Ingredient | Amount [%] w/w |
| --- | --- |
| Dimethicone[1] | 42 |
| Cyclomethicone[2] | 30 |
| Cyclopentasiloxane & Dimethiconol[3] | 25 |
| Phenyl trimethicone[4] | 2 |
| Quaternium ™ 80 | 1 |

[1]DC 200 fluid (ex Univar)
[2]DC 345 fluid (ex Univar)
[3]ABIL ™ OSW 5 (ex Goldschmidt)
[4]DC 556 Fluid (ex Univar)

The leave-on formulation is prepared by mixing the microcapsules at 2% by weight, relative to the total weight of the hair cream, into the formulation prepared above. To another sample of the body wash is added a proprietary fragrance of the type in the capsules, such that the quantity of fragrance added is the same.

The two formulations are applied to hair swatches in an amount of 0.5 g with a micropipette, and hair is massaged using a finger on the whole surface for 10 sec.

The perfume intensity is evaluated on a blind basis after 4 hours by an expert panel consisting of 8 trained panellists. The panellists find that the odour in both cases is weak and of the same intensity. However, rubbing the hair swatch with the capsules produces a noticeable boost in fragrance.

EXAMPLE 8

Preparation of a Rim Block Comprising the 10-Layer PMAA/PVP Microcapsules of Example 2

A toilet rim block gel formulation is prepared by admixing the ingredients listed below.

| Ingredient | Amount [%] w/w |
| --- | --- |
| Natrosol ™ 250 MR | 1 |
| 1,2-Propylene glycol | 4 |
| Emulgin ™ HF 70 | 16.7 |
| Kathon ™ CG | 0.05 |
| Fragrance 1 | 3.5 |
| Water | 74.75 |

A rim block gel is prepared by mixing microcapsules containing a proprietary fragrance 2 (different from the fragrance 1 in the formulation above) at 2% by weight relative to the total weight of the rim block into the rim block formulation prepared above. To another rim block with the same formulation (also containing Fragrance 1) is added proprietary fragrance 2 (which is different from the free fragrance) of the type in the capsules, such that the quantity of fragrance added is the same.

The rim blocks gels are applied to separate toilets.

The perfume is evaluated by an expert panel consisting of 8 trained panellists on a blind basis before and after putting the rim block in contact with water (pH 7).

In the case of the rim block without capsules, the panellists found that the perfume is the same before and after putting the rim block in contact with water for in the absence of microcapsules.

In the case of the rim block with microcapsules, perfume is significantly different before and after putting the rim block in contact with water due to breakage of capsules by pH increase, caused by the toilet water (pH7).

The invention claimed is:

1. A method of encapsulating a liquid active by the application of successive polymer solutions to the liquid active, the method comprising the steps of:
   first, forming a dispersion of the liquid active in an aqueous medium, and, subsequently building successive layers upon the liquid active by successive addition thereto of a series of aqueous polymeric solutions, such that a series of polymer layers are built upon the liquid active, each layer being hydrogen-bonded to the preceding layer, such that
   (i) one of the first two layers is a polycarboxylic acid;
   (ii) the first two layers comprise a combination of polymers selected from poly(methacrylic acid)/poly(vinyl pyrrolidone), poly(acrylic acid)/poly(vinyl pyrrolidone), poly(vinyl acetate)/ethylene-maleic anhydride copolymer and poly(vinyl alcohol)/ethylene-maleic anhydride copolymer; and
   (iii) the first two to four layers taken together exhibit an interfacial compression dilation modulus of greater than 10 mN/m.

2. A method according to claim 1, in which the first two layers are poly(methacrylic acid)/poly(vinyl pyrrolidone).

3. A method according to claim 1, in which the aqueous polymeric solutions are applied in excess, and the remainder washed away, prior to the application of a next layer.

4. A method according to claim 1, in which the polymer shell is crosslinked.

5. A method according to claim 4, in which the polymers comprise amino or hydroxyl groups, and crosslinking is achieved by the addition of a crosslinking material.

6. A method according to claim 1, in which the polymer shell is provided with a final layer of silicate.

7. A method according to claim 6, in which a silicate layer is provided by the hydrolysis of $(R)_n Si(ROH)_{4-n}$ in which R is $C_1$-$C_3$ alkyl and n=1-4, and the addition of the hydrolysis product to the aqueous slurry of capsules.

8. A method according to claim 1, in which further materials are deposited on the polymer shell.

9. A method according to claim 8, in which the further materials are selected from: aminoplast, polyurea, polyurethane, polyacrylic and inorganic materials.

10. The method of claim 1, wherein the first two to four layers taken together exhibit an interfacial compression dilation modulus of greater than 20 mN/m.

11. A method according to claim 5, wherein the crosslinking agent is selected from one or more of: an amine, a glutaraldehyde, an isocyanate, an epoxide and a silicate coupling agent.

12. The method of claim 1, wherein the liquid active is non-sacrificial.

13. A method of encapsulating a liquid droplet of a non-sacrificial liquid active material in an aqueous dispersion, which method excludes a process step of removal of a sacrificial core from within microencapsulation layers during the method, the method comprising the steps of:
  (a) dispersing the non-sacrificial liquid active in an aqueous medium having a pH of less than 6 to provide a core upon which two or more polymeric shell layers are formed;
  (b) causing the formation on this dispersed liquid active of a polymer shell, the formation comprising the sequential deposition of a series of polymeric layers, each layer being capable of hydrogen bonding with the preceding layer;
to form an aqueous slurry of liquid active-containing capsules;
  wherein one of the first two layers is a polycarboxylic acid and that the first two to four layers taken together exhibit an interfacial compression dilation modulus of greater than 10 mN/m; and,
  further wherein, the first two layers comprise a combination of polymers selected from: poly(methacrylic acid)/poly(vinyl pyrrolidone), poly(acrylic acid)/poly(vinyl pyrrolidone), poly(vinyl acetate)/ethylene-maleic anhydride copolymer and poly(vinyl alcohol)/ethylene-maleic anhydride copolymer.

14. The method of claim 1, wherein the thickness of the capsule shell surrounding a liquid active core is 5-100 nm.

15. The method of claim 14, wherein the thickness of the capsule shell surrounding a liquid active core is 5-70 nm.

16. The method of claim 14, wherein the thickness of the capsule shell surrounding a liquid active core is 5-50 nm.

* * * * *